(12) United States Patent
Rosenbloom

(10) Patent No.: US 6,753,325 B2
(45) Date of Patent: Jun. 22, 2004

(54) COMPOSITION AND METHOD FOR PREVENTION, REDUCTION AND TREATMENT OF RADIATION DERMATITIS

(75) Inventor: Richard Allen Rosenbloom, Elkins Park, PA (US)

(73) Assignee: The Quigley Corporation, Doylestown, PA (US)

(*) Notice: Subject to any disclaimer, the term of this patent is extended or adjusted under 35 U.S.C. 154(b) by 0 days.

(21) Appl. No.: 09/993,003

(22) Filed: Nov. 6, 2001

(65) Prior Publication Data

US 2003/0103953 A1 Jun. 5, 2003

(51) Int. Cl.$^7$ .......................... A61K 31/59; A01N 25/00
(52) U.S. Cl. ........................ 514/167; 514/904; 514/905
(58) Field of Search ................................ 514/167, 904, 514/905; 424/59, 60

(56) References Cited

U.S. PATENT DOCUMENTS

| | | | |
|---|---|---|---|
| 4,617,187 A | | 10/1986 | Okuyama et al. .......... 424/94.1 |
| 5,571,441 A | | 11/1996 | Andon et al. ................ 252/1 |
| 5,804,168 A | | 9/1998 | Murad ......................... 424/59 |
| 5,876,737 A | * | 3/1999 | Schonrock et al. ......... 424/401 |
| 5,952,391 A | * | 9/1999 | Gers-Barlag et al. ....... 514/685 |
| 5,972,359 A | * | 10/1999 | Sine et al. ................... 424/401 |
| 5,998,394 A | | 12/1999 | Voorhees et al. ........... 514/167 |
| 6,048,886 A | * | 4/2000 | Neigut ........................ 514/412 |
| 6,162,801 A | * | 12/2000 | Kita ............................ 514/167 |
| 6,296,861 B1 | | 10/2001 | Perricone .................... 424/401 |

FOREIGN PATENT DOCUMENTS

| JP | WO97/18817 | * | 5/1997 | .......... A61K/31/59 |
|---|---|---|---|---|

OTHER PUBLICATIONS

The Merck Manual, 16$^{th}$ ed., 1992, p. 2456–2457.*
"Sports Medicine Articles" [online], Sep. 1, 2000 [retrieved on Jan. 10, 2002]. Retrieved from the Internet:<http://www.rehabnet.com/Sports/Actinic%20Dermatitis.htm>, p. 1–2.*
Reuters, OncoLink—University of Pennsylvania Cancer Center, "OncoLink Cancer News", "Burn Cream Reduces Skin Toxicity During Radiation Therapy for Breast Cancer", Sep. 22, 2000 2pgs.
CancerNews—Willis–Knighton Department of Radiation Oncology, "Skin Care During Radiation Treatment", Feb. 8, 2001.
Shimoi et al., Mutat Res. "Radioprotective effects of antioxidative plant flavonoids in mice", Feb. 19; 350(1):153–61.

William F. Dial, Cosmetic Dermatology, "Topical Vitamin C May Help Protect Skin From UV Damage", Dec. 1991, pp. 34–35.
Bernard Idson, College of Pharmacy, University of Texas at Austin, Ultraviolet Irradiation Injury and Repair, Jan. 1992, pp. 22–24 and pp. 81–81.
Bissett et al., J. Soc. Cosmet. Chem., "Protective effect of a topically applied anti–oxidant plus an anti–inflammary agent against ultraviolet radiation–induced chronic skin–damage in the hairless mouse", 43, Mar./Apr. 1992, pp. 85–92.
Darr et al., British Journal of Dermatology, "Topical vitamin C protects porcine skin from ultraviolet radiation–induced damage" (1992) 127, 247–253.
Dermatology Times, "New Aqueous Vitamin C blocks UV rays" 1991.
Fuchs et al., "Acute Effects of Near Ultraviolet and Visible Light on the Cutaneous Antioxidant Defense System"Oct. 3, 1988, pp. 739–744.
Vitamin E (Tocopherol) vs. Vitamin E Acetate, Roche, Jun. 1991.
Schmuth, et al., "Permeability barrier function of skin exposed to ionizing radiation" Arch Dermatol Aug. 2001; 137(8);1019–23.
Katiyar, et al., "Green tea polyphenol (–)–epigallocatechin–3–gallate treatment of human skin inhibits ultraviolet radiation–induced oxidative stress" Carcinogenesis Feb. 2001; 22(2):287–94.

* cited by examiner

Primary Examiner—Sreeni Padmanabhan
Assistant Examiner—San-ming Hui
(74) Attorney, Agent, or Firm—Knoble Yoshida & Dunleavy, LLC

(57) ABSTRACT

A composition for the preventing, reducing or treating radiation dermatitis includes a mixture of one or more compounds that regulates cell differentiation and/or cell proliferation, and one or more antioxidants formulated in a pharmaceutically acceptable carrier. The composition of the present invention may further include a flavonoid. A method for the topical administration of the composition in accordance with the present invention for the purpose of preventing, reducing or treating radiation dermatitis involves topically administering an effective amount of the composition of the invention an area of skin which has been or will be exposed to radiation. The composition and method can be employed to prevent, reduce or treat radiation dermatitis caused by a wide variety of types of radiation exposure and is particularly useful for the prevention, reduction or treatment of radiation recall dermatitis.

9 Claims, No Drawings

COMPOSITION AND METHOD FOR PREVENTION, REDUCTION AND TREATMENT OF RADIATION DERMATITIS

BACKGROUND OF THE INVENTION

1. Field of the Invention

The present invention relates to a composition and method for preventing, reducing and treating radiation dermatitis.

2. Description of the Prior Art

One common effect of radiation exposure is a condition called radiation dermatitis, in which the skin in the exposed area begins to look reddened, irritated or burned. The exposed skin may also develop a moist reaction, especially where there are skin folds, and may become very sore. Patients receiving radiation therapy are especially at risk for radiation dermatitis. Radiation recall dermatitis has been identified as a particularly bad problem for patients receiving a combination of radiation therapy and chemotherapy to treat cancer.

Many attempts have been made to reduce, control or cure radiation dermatitis. U.S. Pat. No. 4,617,187 to Okuyama, et al. discloses a method for treating radiation dermatitis by topically applying ubidecarenone. However, ubidecarenone might be toxic and can cause many side effects during the treatment.

In some cases, medical care-givers use aquaphor or other products such as carasyn gel and lanolin to partially alleviate radiation dermatitis. It also has been reported that gels containing aloe vera extract can reduce or relieve radiation dermatitis. However, their effectiveness is still questionable.

Some studies have shown that epidermal permeability barrier function is impaired in patients who exhibit clinical signs of radiation dermatitis. The studies have also suggested that preservation of the epidermal permeability barrier function by topical treatment may ameliorate radiation dermatitis.

There still remains a need in the art for effective compositions and methods to prevent, reduce and treat radiation dermatitis.

Accordingly, it is an objective of certain embodiments of the present invention to provide a topical composition that, when applied to a skin area, will prevent, reduce or treat radiation dermatitis caused by exposure of that skin area to radiation.

It is another objective of certain embodiments of the present invention to provide a method to effectively prevent, reduce or treat radiation dermatitis.

It is further an objective of certain embodiments of the present invention to provide a composition for preventing, reducing or treating radiation dermatitis, which does not cause severe side effects to a patient treated with the composition.

These and other objects of the present invention will be apparent from the summary and detailed descriptions of the invention which follow.

SUMMARY OF THE INVENTION

In a first aspect, the present invention relates to a topical composition for preventing, reducing or treating radiation dermatitis. The composition includes a mixture of a compound that regulates cell differentiation and/or cell proliferation, and an antioxidant.

In a second aspect, the present invention relates to a method for the topical administration of a composition in accordance with the present invention for preventing, reducing or treating radiation dermatitis. In the method, an effective amount of the composition of the present invention is topically administered to an area of skin to prevent, reduce or treat radiation dermatitis caused by exposure of that area of skin to radiation.

DETAILED DESCRIPTION OF THE PREFERRED EMBODIMENTS

In a first aspect, the present invention relates to a topical composition for preventing, reducing or treating radiation dermatitis. The composition includes a mixture of a compound that regulates cell differentiation and/or cell proliferation, and an antioxidant.

The compound that regulates cell differentiation and/or cell proliferation may be selected from suitable compounds that have this activity. Suitable compounds that regulate cell differentiation and/or cell proliferation are those that do not induce significant, adverse side effects when topically applied to a patient in amounts that regulate cell differentiation and/or cell proliferation, and which do not react with one or more of the ingredients of the topical composition resulting in a substantial loss of activity of one or more active ingredients. Preferred compounds for regulating cell differentiation and/or cell proliferation are those that occur naturally in the human body and/or materials obtained from plants or animals which may be topically applied by humans without significant, adverse side effects in the amounts used, or derivatives thereof.

More preferably, the compounds that regulate cell differentiation and/or cell proliferation used in the present invention further inhibit or prevent cell differentiation or cell proliferation. Even more preferably, the compounds that regulate cell differentiation and/or cell proliferation used in the present invention accomplish at least one of the following: maintain the cellular homeostasis and normal cell metabolism, regulate cell differentiation, work synergistically with vitamin A to induce certain cancer cells to differentiate into normal cells, help maintain the epidermal permeability barrier, inhibit cancer cell differentiation, inhibit cancer cell proliferation.

Exemplary compounds that regulate cell differentiation and/or cell proliferation are vitamin $D_3$, vitamin $D_3$ analogs, compounds that may be converted or metabolized into vitamin $D_3$ in the human body, and metabolites thereof. Exemplary compounds that may be converted or metabolized into a vitamin $D_3$ include common cholesterols illustrated below. The cholesterol illustrated below may be converted into Provitamin D when a hydrogen is removed from the number 7 carbon, which then forms a double bond with the number 8 carbon, in the second, or 'B' ring of the cholesterol molecule. The cholesterol is 'oxidized' (that is, an electron is removed with the hydrogen atom), so that the double bond is a consequence of 2 mutually shared electrons between carbons 7 and 8.

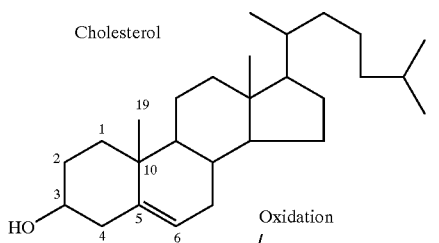

Cholesterol

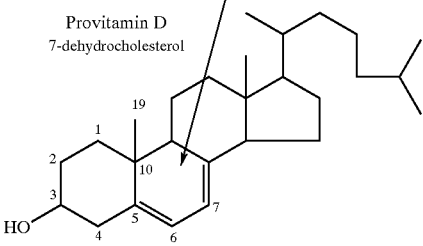

Provitamin D
7-dehydrocholesterol

Provitamin D may be converted to Vitamin $D_3$ by the action of ultraviolet light through our skin. In this reaction, the B ring of the sterol molecule is opened.

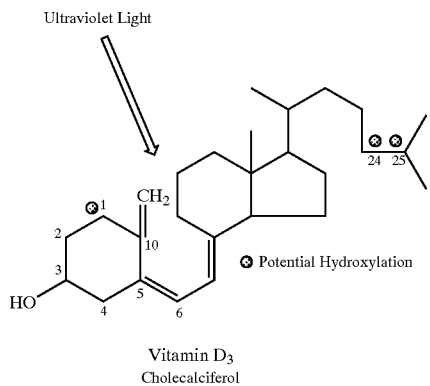

Vitamin $D_3$
Cholecalciferol

Cholecalciferol, which is Vitamin $D_3$, may be further converted into another vitamin D intermediate, 25-hydroxycholecalciferol, in the liver by mitochondrial hydroxylase, in the presence of NADPH, and molecular oxygen.

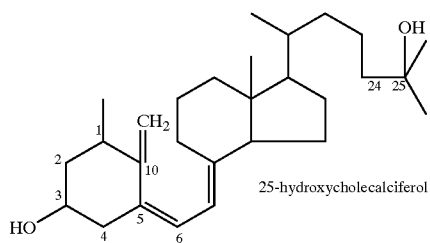

25-hydroxycholecalciferol

When more active vitamin $D_3$ is required, 25-hydroxycholecalciferol is transported to the kidney where a new hydrolase enzyme is synthesized. This enzyme introduces another hydroxyl group at position 1, and the bioactive form of Vitamin $D_3$, calcitriol, is produced.

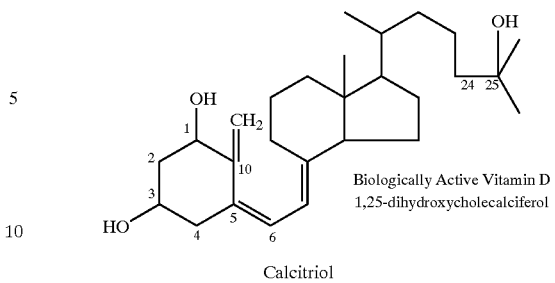

Biologically Active Vitamin D
1,25-dihydroxycholecalciferol

Calcitriol

Exemplary vitamin $D_3$ analogs include 1(S), 3(R)-dihydroxy-20(R)-(1-ethoxy-5-ethyl-5-hydroxy-2-heptyn-1-yl)-9, 10-seco-pregna-5(Z), 7(E), 10 (19)-triene. Exemplary vitamin $D_3$ metabolites include vitamin $D_3$ 1, 25-dihydroxyvitamin $D_3$, which is a metabolite of vitamin $D_3$. Also, pharmaceutically acceptable salts of the compounds that regulate cell differentiation and/or cell proliferation may be employed. The most preferred compound that regulates cell differentiation and/or cell proliferation is vitamin $D_3$.

The compound that regulates cell differentiation and/or cell proliferation is used in an amount effective to regulate cell differentiation and/or cell proliferation when applied topically to the skin in the composition of the present invention.

In order to formulate the compound that regulates cell differentiation and/or cell proliferation in the topical composition of the present invention, it may be necessary to use a dispersant. Suitable dispersant materials are known to persons skilled in the art. A particularly suitable dispersant for the compound that regulates cell differentiation and/or cell proliferation is corn oil. Corn oil also has the advantage that it is a natural product. The amount of corn oil used is an amount sufficient to disperse the compound that regulates cell differentiation and/or cell proliferation.

Another ingredient in the composition of the present invention is the antioxidant. The antioxidant may be a single compound or a mixture of two or more compounds. Compounds which may be used as antioxidants are those which exhibit antioxidant activity when administered topically without causing any severe adverse side affects when used in an amount effective to provide sufficient antioxidant activity, and which do not react with one or more of the ingredients of the topical composition resulting in a substantial loss of activity of one or more active ingredients. Preferred antioxidants are those that occur naturally in the human body and/or materials obtained from plants or animals which may be topically applied by humans without significant, adverse side effects in the amounts used, or derivatives thereof.

Preferred antioxidants are selected from ascorbyl palmitate, ascorbic acid (vitamin C), vitamin A, vitamin E acetate, α-lipoic acid, especially DL-α-lipoic acid, coenzyme Q10, glutathione, (−)-epigallocatechin-3-gallate, catechin, galangin, rutin, luteolin, morin, fisetin, silymarin, apigenin, gingkolides, hesperitin, cyanidin, citrin, curcuminoid and derivatives thereof which exhibit antioxidant activity. Even more preferably, mixtures of two or more antioxidants are employed in the composition of the present invention. Particularly preferred antioxidant mixtures are ascorbyl palmitate with one or more of vitamin A, vitamin E acetate and α-lipoic acid especially DL-α-lipoic acid. Derivatives of one or more of these compounds which exhibit antioxidant activity when administered topically may also be employed. The antioxidants may also be used in the form of their pharmaceutically acceptable salts and this may be preferred in some cases to increase solubility or dispersability, to reduce adverse side effects, etc. By "structurally similar derivatives" is meant that the compound exhibits antioxidant activity and contains at least one significant, common structural element with the compound from which it is derived.

In another preferred embodiment, the antioxidant used in the composition of the present invention may be partially or completely replaced with an amount of one or more antioxidant enzymes having a comparable level of activity. The antioxidant enzymes useful in the present invention are those capable of scavenging radicals, promoting radical scavengers or preventing radical formation. More preferably, the antioxidant enzyme used in the present invention is skin absorbable. The preferred antioxidant enzyme useful in the present invention includes superoxide dismutase, catalase, glutathione peroxidase, methionine reductase and equivalents thereof. These antioxidant enzymes may prevent the formation of free radicals or scavenge the formed free radicals to prevent cell damage. In addition, one or more of these antioxidant enzymes may act synergistically with one or more of the antioxidants in the composition to scavenge free radicals more effectively to prevent cell damage in the skin.

The antioxidant component of the composition is used in an amount effective to provide significant antioxidant activity when applied topically to the skin in the composition of the present invention.

The ratio of the amount of the compound that regulates cell differentiation and/or cell proliferation to the amount of antioxidant employed in the compositions of the present invention is from about 200 IU per gram of antioxidant to about 3 million IU per gram of antioxidant. More preferably, about 1800 IU per gram of antioxidant to about 1 million IU per gram of antioxidant, and, most preferably about 5000 IU per gram of antioxidant to about 200,000 IU per gram of antioxidant of the compound that regulates cell differentiation and/or cell proliferation is employed.

The antioxidants used in the composition of the present invention are preferably selected not only for their antioxidant activity, but also based on other beneficial effects that particular compounds may provide. For example, a racemic mixture of $\alpha$-lipoic acid not only has a strong antioxidant activity but also has a recycling effect on vitamin C and E, and thus is a particularly preferred antioxidant for the present invention. In addition, $\alpha$-lipoic acid can function in both lipid and non-lipid environments. Similarly, vitamin E may also contribute to an anticancer effect and have a beneficial effect on the skin and is thus a preferred antioxidant. Vitamin A (retinol or retinyl ester) may also have anticancer effects. Vitamin A is also a fat-soluble material and thus is preferred for use due to this additional beneficial property. However, due to its solubility characteristics, vitamin A may need to be formulated in a suitable dispersant such as corn oil in much the same manner as vitamin $D_3$ as described above.

Preferably, the vitamins A and $D_3$ used in the composition of the present invention may be formulated in a single corn oil dispersion. Generally, every cubic centimeter (cc) of the corn oil dispersion of vitamins A and $D_3$ used in the present invention may contain about 500,000 to about 2,000,000 IU of vitamin A and about 50,000 to about 200,000 IU of vitamin $D_3$. Preferably, every cc of the corn oil dispersion of vitamins A and $D_3$ used in the present invention may contain about 1,000,000 IU of vitamin A and about 100,000 IU of vitamin $D_3$.

Preferably, the antioxidant used in the composition of the present invention includes a combination of effective amounts of vitamin A, vitamin C or its ester, vitamin E and $\alpha$-lipoic acid to achieve the beneficial effect of recycling vitamin C or its ester and vitamin E by $\alpha$-lipoic acid.

Preferably, the composition of the present invention further includes a flavonoid and/or flavonoid derivative which may have radioprotective effects. In addition, flavonoids and/or flavonoid derivatives such as quercetin may have other beneficial effects such as anti-inflammatory and maintaining structural integrity of ischemic or hypoxic tissue, which may occur after radiation exposure. Exemplary flavonoids and flavonoid derivatives include (−)-epigallocatechin; (−)-epigallocatechin-gallate; 1,2,3,6-tetra-o-gallyol-β-d-glucose; 2'o-acetylacetoside; 3,3',4-tri-o-methyl-ellagic acid; 6,3',4'-trihydroxy-5,7,8-trimethoxyflavone; 6-hydroxy-luteolin; 6-hydroxykaempferol-3,6-dimethyl ether; 7-o-acetyl-8-epiloganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; chrysin-5,7-dihydroxyflavone; chrysoeriol; chrysosplenol; chrysosplenoside-a; chrysosplenoside-d; cosmosiin; δ-cadinene; dimethylmussaenoside; diacerylcirsimaritin; diosmetin; dosmetin; ellagic acid; ebinin; ethyl brevifolin carboxylate; flavocannibiside; flavosativaside; genistein; gossypetin-8-glucoside; haematoxylin; hesperidine; hispiduloside; hyperin; indole; iridine; isoliquiritigenin; isoliquiritin; isoquercitrin; jionoside; juglanin; kaempferol-3-rhamnoside; kaempferol-3-neohesperidoside; kolaviron; licuraside; linariin; linarin; lonicerin; luteolin; luetolin-7-glucoside; luteolin-7-glucoside; luetolin-7-glucoronide; macrocarpal-a; macrocarpal-b; macrocarpal-d; macrocarpal-g; maniflavone; methy scutellarein; naringenin; naringin; nelumboside; nepetin; nepetrin; nerolidol; oxyayanin-a; pectolinarigenin; pectolinarin; quercetagetin; quercetin; quercimertrin; quercitrin; quercitryl-2" acetate; reynoutrin; rhamnetin; rhoifolin; rutin; scutellarein; sideritoflavone; sophoricoside; sorbarin; spiraeoside; trifolin; vitexin; and wogonin.

The most preferred flavonoids and/or flavonoid derivatives are quercetin, quercetrin, myricetin, kaempferol and myrecetrin since these compounds may have some anti-inflammatory activity and/or may help stabilize cell membranes in combination with a relatively low toxicity, both of which activities may be beneficial in the treatment of radiation dermatitis. Also, pharmaceutically acceptable salts of these flavonoids and/or flavonoid derivatives may be employed. The particular flavonoid and/or flavonoid derivative included in the composition may be determined by factors such as toxicity, bioavailability, solubility or dispersability, among others.

The particular flavonoids and flavonoid derivatives are also preferred since some of these compounds may provide additional beneficial effects in the composition of the present invention. For example, quercetin may also have an anti-oxidative and anticlastogentic effect. It may prevent the decrease of endogenous ascorbic acid (vitamin C) in bone marrow after gamma-ray irradiation. In addition, some of the flavonoids and flavonoid derivatives may act as a radical scavenger to scavenge free radicals such as hydroxyl radicals to enhance their radioprotective effects.

In a more preferred embodiment, both quercetin and ascorbyl palmitate are included in the composition of the present invention because there seems to be an enhanced anti-oxidative effect of the combination of quercetin and ascorbyl palmitate.

The flavonoid or flavonoid derivative is used in an amount of about 0.02 to about 2 grams per gram of the antioxidant in the composition. More preferably, the flavonoid or flavonoid derivative is employed in an amount of about 0.05 to about 1 gram and most preferably an amount of 0.1 to about 0.4 grams per gram of the total antioxidant in the composition.

The compositions in accordance with the present invention may provide one or more of the following beneficial effects to a patient when topically applied in effective amounts: antioxidant properties, free radical scavenging, transition metal chelation, nitric oxide stabilization, anti-inflammatory activity, relief of pain, burning, tingling, electrical sensations and/or hyperalgesia, increased microcirculation, nitric oxide stabilization, promotion of healing of skin ulcers and lesions, protein kinase C inhibition, decreased oxidative stress, anti-inflammation, protection against radiation damage, blockage of the formation of leukotrienes, stabilization of cell membranes, and regulation of cell differentiation and/or cell proliferation.

The compositions of the present invention are preferably formulated in a pharmaceutically acceptable carrier. The pharmaceutically acceptable carrier used in the present invention may be a carrier suitable for use as a carrier for topical compositions wherein the active ingredients, which may include the one or more compounds that regulate cell differentiation and/or cell proliferation, one or more antioxidants, and preferably one or more flavonoids and flavonoid derivatives, are dissolved, dispersed and/or suspended in the composition. Exemplary carriers may include creams, ointments, lotions, pastes, jellies, sprays, aerosols, bath oils, and other pharmaceutical carriers which accomplish direct contact between the active ingredients of the composition of the present invention and the pore of the skin. Preferably, the pharmaceutically acceptable carrier may make up more than about 80%, and more preferably about 80–95% w/w of the total composition. In some cases, it may be necessary to dissolve one or more the active ingredients in an appropriate solvent such as ethanol or DMSO (dimethylsulfoxide), and the like, to facilitate the incorporation of the one or more active ingredients into the composition or the pharmaceutically acceptable carrier.

One preferred carrier of the present invention contains at least a hydrophilic ointment base, panthenol or a panthenol derivative and a dispersant if needed to disperse one or more insoluble or partially insoluble active ingredients in the carrier. Another preferred carrier of the present invention employs hydroxymethyl cellulose as the carrier material.

Yet another preferred pharmaceutically acceptable carrier may include a solution of an acrylic copolymer in a non-aqueous solvent system which mainly contains polyethylene glycol such as methoxy polyethylene glycol 550 (MPEG). A particular preferred MPEG is SENTRY CARBOWAX™ MPEG 550 sold by Union Carbide, which is a food/pharmaceutical/cosmetic grade material. Polyethylene glycols are generally non-toxic, water-soluble polymers that are fully biodegradable. In the solution, the acrylic copolymer would preferably be present in a concentration range of 3–6% by weight. Preferably, the acrylic copolymer has a molecular weight of more than 20,000. More preferably, the acrylic copolymer has a molecular weight of more than 100,000 so that it would not be systematically absorbed by a human body or skin.

Suitable hydrophilic ointment bases are known to persons skilled in the art. Exemplary hydrophilic ointment bases suitable for use in the present invention are non-U.S.P. hydrophilic ointment bases such as those made by Fougera, Inc. Sufficient hydrophilic ointment base is employed to act as a carrier for the active ingredients of the composition. Typically, the hydrophilic ointment base will make up more than about 80% of the total composition, and more preferably about 80–95% of the composition is the hydrophilic ointment base. The hydrophilic ointment base functions as a carrier and enhances penetration into the skin. Similar proportions of the hydroxymethyl cellulose-based carrier or acrylic copolymer solution based carrier may also be employed.

The panthenol or panthenol derivatives useful in the present invention include at least D-panthenol, DL-panthenol and mixtures thereof. This component of the carrier has skin moisturizing properties and acts as a quick, deep penetrating component of the carrier that helps deliver the active ingredients through the skin to the area to be treated and may also impart a healing effect to damaged tissue. The amount of panthenol or panthenol derivative to be employed is from about 0.25 to about 10 weight percent, more preferably from about 0.5 to about 5 weight percent and most preferably from about 1 to about 2 weight percent, based on the total weight of the composition.

The carrier of the present invention may also include additional ingredients such as other carriers, moisturizers, humectants, emollients, dispersants, radiation blocking compounds, particularly UV-blockers, as well as other suitable materials that do not have a significant adverse effect on the activity of the topical composition. Preferred additional ingredients for inclusion in the carrier are sodium acid phosphate moisturizer, witch hazel extract, glycerine humectant, apricot kernal oil emollient, and corn oil dispersant.

Other materials which may optionally be included in the topical compositions of the present invention include inositol, other B-complex vitamins, and anti-inflammatory agents such as $\gamma$-linolenic acid. The composition of the present invention may also be employed to facilitate wound healing, for the treatment of skin cancer and/or one or more symptoms thereof, or as a composition for protecting skin from the harmful effects of radiation, such as radiation breakdown or radiation recall dermatitis.

The composition of the present invention is preferably made by cold compounding. This may be an important feature of the invention if one or more of the compounds employed in the topical composition are sensitive to heat or other types of energy in which case the activity of the composition may be detrimentally affected as a result of the formulation of the compositions in another manner. Thus, the ingredients of the topical composition the present invention are preferably mixed together, without heating using a sufficient amount of the carrier to provide a substantially homogeneous cream or ointment. It may be necessary to dissolve, disperse or suspend one or more of the ingredients prior to cold compounding in order to ensure substantially homogeneous distribution of the active ingredients in the composition.

A preferred pharmaceutically acceptable carrier composition of the invention can be made using the following ingredients, all based on use of one pound of hydrophilic ointment base. 25–35 parts of a 50% aqueous solution of sodium acid phosphate moisturizing agent, 5–10 parts of D- or DL-panthenol, 5–10 parts of glycerine, 1–3 parts of apricot kernal oil and 10–20 parts of witch hazel extract. Particularly preferred combinations of antioxidants, a flavonoid and a compound which regulates cell differentiation and/or cell proliferation for use in the present invention comprises or consists especially of 2–9 parts of a dispersion of vitamins A and $D_3$ in a corn oil base, 1–4 parts of quercetin, 1–4 parts of vitamin E acetate, 2–4 parts of ascorbyl palmitate and 0.25–2 parts of α-lipoic acid. Optionally, one or more of the optionally ingredients of the composition such as glycerin, witch hazel extract, vitamins A and E and/or the ascorbyl palmitate can be reduced or eliminated from a particular composition, if desirable, or larger amounts of one type of component, i.e. an antioxidant, can be employed while reducing the amount of another component of the same type or having a similar activity.

In a second aspect, the present invention relates to a method for the topical administration of a composition in accordance with the present invention for the purpose of preventing, reducing or treating radiation dermatitis. The method of the present invention includes the step of topically applying a composition of the present invention to an area of skin prior to, during or after exposure of that area of skin to radiation. In the method, an effective amount of the composition of the invention is applied to the skin one to six times daily, as needed, to the skin.

For prevention or reduction of radiation dermatitis, the composition is preferably applied to the skin before exposure to radiation. More preferably, the composition of the present invention is applied to the skin at least once twenty-four hours before the start of the radiation exposure, and three times (e.g., morning, noon and bedtime) in the 24 hour period immediately before the radiation exposure. For each application, it is preferable to apply an amount of the composition which is sufficient to cover the area of the skin to be exposed to radiation with a thin layer of the composition. The composition should preferably be rubbed into the skin until little or no residue remains on the skin.

In a method for treating or reducing radiation dermatitis, an effective amount of the composition of the invention is applied one to six times daily, as needed, to an area of skin inflicted with radiation dermatitis. In the method, a thin layer of the composition is preferably applied to the inflicted area of skin, as needed, and the composition should preferably be rubbed into the skin until little or no residue remains on the skin.

The method of the present invention may provide one or more of the beneficial effects described above for the compositions of the invention. In addition, the method of the present invention may provide one or more additional beneficial effects due to one or more of the ingredients contained in the pharmaceutically acceptable carrier as described above.

The compositions and methods of the present invention may be employed to treat radiation dermatitis resulting from exposure to one or more of proton radiation, fluoroscopic radiation, ultraviolet radiation, alpha radiation, beta radiation and gamma radiation. The invention is particularly useful for persons who are, or will be, undergoing treatment which may result in exposure of an area of the skin to radiation. Also, the invention can be employed to treat persons exposed to radiation as a result of a radiation attack, a nuclear accident or other radiation exposure.

A particularly preferred application of the method of the present invention is for the purpose of preventing, reducing or eliminating radiation recall dermatitis which frequently results from a combination of radiation therapy and chemotherapy.

The invention will now be further illustrated by the following example.

EXAMPLE 1

A topical composition including a mixture of an hydrophilic ointment base, sodium acid phosphate moisturizing agent, a witch hazel extract carrier, glycerine, apricot kernal oil and DL-panthenol, as the pharmaceutically acceptable carrier and vitamins A and $D_3$, ascorbyl palmitate, α-lipoic acid and vitamin E acetate as the active ingredients which have antioxidant properties and/or regulate cell differentiation and/or cell proliferation was prepared by cold compounding. The formulation of the composition is given in Table 1.

The composition was prepared by first placing the hydrophilic ointment base in a stainless steel bowl and mixing briskly until the ointment becomes creamy. Then, the sodium acid phosphate, panthenol, ascorbyl palmitate, glycerine, apricot kernal oil, vitamins A and $D_3$, quercetin, witch hazel extract, vitamin E acetate and α-lipoic acid were added in that order. After each ingredient was added, mixing was continued until all traces of dry ingredients disappeared and a substantially homogeneous mixture was obtained. The final color should be a consistent yellow and the cream should have the consistency of cake frosting. The mixture was then placed in a sterile container. All containers which contact the composition during mixing must also be sterilized with, for example, zephiran chloride or a Clorox® solution such as betadine.

This composition was topically administered, under the supervision of a physician, to several patients a day before undergoing radiation therapy treatment. The administration of the composition was carried out by applying a thin film of the composition to the areas of the skin to be exposed to radiation. The topical composition was applied three times during that day in the morning, noon and at bedtime. All of the patients administered with the composition of the present invention experienced much less severe radiation dermatitis after radiation therapy than patients who were not treated with the composition of the invention. The effects noted by the patients included reductions in burning, irritation and redness in the areas of skin that were treated.

TABLE 1

| Ingredient | Amount Employed |
| --- | --- |
| Hydrophilic ointment base | 1 pound |
| 50% aqueous solution of Sodium acid phosphate | 25 cc |
| DL-panthenol | 5 cc |
| Glycerine | 5 cc |
| Apricot kernal oil | 3 cc |
| Witch hazel extract | 12 cc |
| α-Lipoic acid | 500 mg |
| Vitamin E acetate | 2 cc |
| Vitamin A and $D_3$ dispersion in corn oil | 6 cc |
| Ascorbyl Palmitate | 2 grams |
| Quercetin | 2 grams |

EXAMPLE 2

Tables 2–6 below exemplify some of the alternative formulations according to the present invention without listing all of the ingredients in the pharmaceutically acceptable carrier. These alternative formulations may be prepared using the same procedure as described in Example 1.

TABLE 2

| Ingredient | Amount Employed |
| --- | --- |
| Ascorbyl Palmitate | 2 grams |
| Hesperidine | 2 grams |
| Rutin | 2 grams |

TABLE 2-continued

| Ingredient | Amount Employed |
| --- | --- |
| Vitamin A and $D_3$ dispersion in corn oil | 3 cc |
| Vitamin E Acetate | 1 cc |
| DL Panthenol | 5 cc |

TABLE 3

| Ingredient | Amount Employed |
| --- | --- |
| Ascorbyl Palmitate | 2 grams |
| Ascorbyl Glucosamine | 1 gram |
| Luteolin | 4 grams |
| Vitamin A and $D_3$ dispersion in corn oil | 3 cc |
| Vitamin E acetate | 1 cc |
| DL Panthenol | 5 cc |

TABLE 4

| Ingredient | Amount Employed |
| --- | --- |
| Ascorbyl Glucosamine | 2 grams |
| Apigenin | 4 grams |
| Vitamin A and $D_3$ dispersion in corn oil | 3 cc |
| Vitamin E acetate | 1 cc |
| DL Panthenol | 5 cc |

TABLE 5

| Ingredient | Amount Employed |
| --- | --- |
| Ascorbyl Palmitate | 2 grams |
| γ-Linolenic acid | 500 mg |
| Rutin | 4 grams |
| Vitamin A and $D_3$ dispersion in corn oil | 3 cc |
| Vitamin E acetate | 1 cc |
| DL Panthenol | 5 cc |

TABLE 6

| Ingredient | Amount Employed |
| --- | --- |
| Ascorbyl Palmitate | 4 grams |
| Quercetin | 2 grams |
| Coenzyme Q10 | 500 mg |
| α-Lipoic acid | 50 mg |
| Vitamin A and $D_3$ dispersion in corn oil | 3 cc |
| Vitamin E acetate | 1 cc |
| DL Panthenol | 5 cc |

The foregoing detailed description of the invention and examples are not intended to limit the scope of the invention in any way and should not be construed as limiting the scope of the invention. The scope of the invention is to be determined from the claims appended hereto.

What is claimed is:

1. A method for the reduction or treatment of at least one adverse effect of radiation dermatitis caused by one or more types of radiation selected from the group consisting of alpha radiation, beta radiation, gamma ray radiation and fluoroscopic radiation, comprising the step of applying to an area of skin which has been or will be exposed to said one or more types of radiation, a topical composition which comprises:

an amount of one or more compounds that inhibit at least one of cell differentiation and cell proliferation selected from the group consisting of vitamin $D_3$; 1(S), 3(R)-dihydxoxy-20(R)-(1-ethoxy-5-ethyl-5-hydroxy-2-heptyn-1-yl)-9, 10-seco-pregna-5(Z), 7(E), 10(19)-triene; 1,25-dihydroxyvitamin $D_3$, and pharmaceutically acceptable salts thereof, which is effective, when administered topically in the topical composition to inhibit at least one of cell differentiation and cell proliferation, and an effective amount of one or more antioxidants or pharmaceutically acceptable salts thereof, formulated in a pharmaceutically acceptable carrier for a topical composition.

2. A method as claimed in claim 1, wherein the one or more compounds that inhibit at least one of cell differentiation and cell proliferation are selected from the group consisting of: cholesterols, 7-dehydrocholestrol, vitamin $D_3$, 1,25-dihydroxyvitamin $D_3$, 1(S), 3(R)-dihydroxy-20(R)-(1-ethoxy-5-ethyl-5-hydroxy-2-heptyn-1-yl)9, 10-seco-pregna-5(Z), 7(E), 10(19)-triene, and 25-hydroxycholecalciferol, calcitriol, and pharmaceutically acceptable salts thereof.

3. A method as claimed in claim 1, wherein the one or more antioxidants are selected from the group consisting of: ascorbyl palmitate, ascorbic acid, vitamin A, vitamin E acetate, α-lipoic acid, coenzyme Q10, glutathione, (-)-epigallocatechin-3-gallate, catechin, galangin, rutin, luteolin, morin, fisetin, silymarin, apigenin, gingkolides, hesperitin, cyanidin, citrin, curcuminoid, and pharmaceutically acceptable salts thereof.

4. A method as claimed in claim 1, wherein the compound that inhibits at least one of cell differentiation and cell proliferation comprises vitamin $D_3$, and the antioxidant comprises vitamin A, vitamin E acetate, and α-lipoic acid.

5. A method as claimed in claim 1, wherein the pharmaceutically acceptable carrier comprises a sufficient amount of at least one non-U.S.P. hydrophilic ointment base to form a topical composition.

6. A method as claimed in claim 5, wherein the pharmaceutically acceptable carrier further comprises a sufficient amount of a panthenol selected from D-panthenol and DL-panthenol to promote penetration of one or more of the antioxidants and compounds which inhibit at least one of cell differentiation and cell proliferation, into the skin.

7. A method as claimed in claim 1, wherein the pharmaceutically acceptable carrier comprises hydroxymethyl cellulose.

8. A method as claimed in claim 1, wherein the pharmaceutically acceptable carrier comprises an acrylic copolymer dissolved in polyethylene glycol.

9. A method as claimed in claim 1 wherein the antioxidant comprises one or more antioxidant enzymes.

* * * * *